(12) United States Patent
Kim et al.

(10) Patent No.: US 10,655,100 B2
(45) Date of Patent: May 19, 2020

(54) METHOD FOR INDUCING ECTODERMAL DIFFERENTIATION OF EMBRYOID BODIES DERIVED FROM HUMAN PLURIPOTENT STEM CELLS BY CXCR2 STIMULATION

(71) Applicant: KOREA UNIVERSITY RESEARCH AND BUSINESS FOUNDATION, Seoul (KR)

(72) Inventors: Byung Soo Kim, Seoul (KR); Ji-Hye Jung, Seoul (KR); Yong Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/936,729

(22) Filed: Nov. 10, 2015

(65) Prior Publication Data
US 2017/0044493 A1    Feb. 16, 2017

(30) Foreign Application Priority Data
Aug. 12, 2015  (KR) .................. 10-2015-0113833

(51) Int. Cl.
| | | |
|---|---|---|
| *C12N 5/073* | (2010.01) | |
| *C07K 14/52* | (2006.01) | |
| *C07K 14/54* | (2006.01) | |
| *C12N 5/0735* | (2010.01) | |

(52) U.S. Cl.
CPC .......... *C12N 5/0603* (2013.01); *C07K 14/522* (2013.01); *C07K 14/5421* (2013.01); *C12N 5/0606* (2013.01); *C12N 2501/21* (2013.01); *C12N 2501/998* (2013.01); *C12N 2506/02* (2013.01); *C12N 2506/45* (2013.01)

(58) Field of Classification Search
CPC ............................ C12N 5/0603; C07K 14/522
See application file for complete search history.

(56) References Cited

U.S. PATENT DOCUMENTS

2010/0075416 A1* 3/2010 Primiano ............. C12N 5/0606
                                                               435/366

OTHER PUBLICATIONS

Nizzardo et al (Cell Mol Life Sci, 67: 3837-3847, 2010).*
Acosta et al, Cell Cycle 7:19, 2956-2959, 2008 (Year: 2008).*
Cai, C., et al., "Directing the differentiation of embryonic stem cells to neural stem cells", "Developmental Dynamics", Dec. 2007, pp. 3255-3266, vol. 236.
D'Amour, K., et al., "Efficient differentiation of human embryonic stem cells to definitive endoderm", "Nature Biotechnology", Oct. 28, 2005, pp. 1534-1541, vol. 23, No. 12.
Jung, J., et al., "CXCR2 and its related ligands play a novel role in supporting the pluripotency and proliferation of human pluripotent stem cells", "Stem Cells and Development", Dec. 23, 2014, pp. 948-961, vol. 24, No. 8.
Jung, J., et al., "CXCR2/MTOR/Beta-Catenin and human telomerase catalytic subunit axis supports human pluripotent stem cells", "Late Breaking Abstracts", Jun. 24-27, 2015, p. 17 (Abstract), International Society for Stem Cell Research 2015 Annual Meeting, Stockholm, Sweden.
Kaspi, H., et al., "Brief report: miR-290-295 regulate embryonic stem cell differentiation propensities by repressing Pax6", "Stem Cells", Oct. 2013, pp. 2266-2272, vol. 31.
Noisa, P., et al., "Identification and Characterisation of the Early Differentiating Cells in Neural Differentiation of Human Embryonic Stem Cells", "PLoS One", May 15, 2012, pp. e37129 (1-11), vol. 7, No. 5.
Takahashi, T., et al., "Ascorbic acid enhances differentiation of embryonic stem cells into cardiac myocytes", "Circulation", Mar. 31, 2003, pp. 1912-1916, vol. 107.
Teo, A., et al., "Pluripotency factors regulate definitive endoderm specification through eomesodermin", "Genes & Development", Jan. 18, 2011, pp. 238-250, vol. 25.
Verfaille, C., "Stem cell plasticity", "Hematology", Feb. 2005, pp. 293-296, vol. 10 Suppl 1.
Zhou, J., et al., "mTOR supports long-term self-renewal and suppresses mesoderm and endoderm activities of human embryonic stem cells", "PNAS", May 12, 2009, pp. 7840-7845, vol. 106, No. 19.
Bento, A., et al., "The Selective Nonpeptide CXCR2 Antagonist SB225002 Ameliorates Acute Experimental Colitis in Mice", "Journal of Leukocyte Biology", Jul. 24, 2008, pp. 1213-1221, vol. 84.
Bradley, M., et al., "SB265610 is an Allosteric, Inverse Agonist at the Human CXCR2 Receptor", "British Journal of Pharmacology", Apr. 27, 2009, pp. 328-338, vol. 158.
Edman, L.C., et al., "a-Chemokines Regulate Proliferation, Neurogenesis, and Dopaminergic Differentiation of Ventral Midbrain Precursors and Neurospheres", "Stem Cells", 2008 pp. 1891-1900, vol. 26, No. 7.

(Continued)

*Primary Examiner* — Anoop K Singh
*Assistant Examiner* — Magdalene K Sgagias
(74) *Attorney, Agent, or Firm* — Hultquist, PLLC; Steven J. Hulquist

(57) ABSTRACT

The present invention relates to a method of inducing the differentiation of human pluripotent stem cell-derived embryoid bodies into ectoderm by CXCR2 stimulation, and more particularly, to a method of promoting the differentiation of human pluripotent stem cell-derived embryoid bodies into ectoderm by stimulating and activating the surface receptor CXCR2 of the embryoid bodies with the CXCR2-specific ligand GRO-α. The method of inducing the differentiation of human pluripotent stem cell-derived embryoid bodies into ectoderm by CXCR2 stimulation according to the present invention can increase the efficiency and utility of stem cells as a cell therapeutic agent, because it promotes the differentiation of stem cells into a specific germ layer serving as the origin of target cells, which is the first important step for inducing the differentiation of stem cells into specific cells.

1 Claim, 5 Drawing Sheets

Specification includes a Sequence Listing.

(56) References Cited

OTHER PUBLICATIONS

Krtolica, A., et al., "GROa regulates human embryonic stem cell self-renewal or adoption of neuronal fate", "Differentiation", Apr. 2011, pp. 222-232; doi:10.1016/j.diff.2011.01.001, vol. 81, No. 4. Note: For the non-patent literature citations that no month of publication is indicated, the year of publication is more than 1 year prior to the effective filing date of the present application.

* cited by examiner

METHOD FOR INDUCING ECTODERMAL DIFFERENTIATION OF EMBRYOID BODIES DERIVED FROM HUMAN PLURIPOTENT STEM CELLS BY CXCR2 STIMULATION

CROSS-REFERENCE TO RELATED APPLICATION

The priority of Korean Patent Application No. 10-2015-0113833 filed Aug. 12, 2015 is hereby claimed under the provisions of 35 USC 119. The disclosure of Korean Patent Application no. 10-2015-0113833 is hereby incorporated herein by reference, in its entirety, for all purposes.

TECHNICAL FIELD

The present invention relates to a method of inducing the differentiation of human pluripotent stem cell-derived embryoid bodies into ectoderm by CXCR2 stimulation, and more particularly, to a method of promoting the differentiation of human pluripotent stem cell-derived embryoid bodies into ectoderm by stimulating and activating the surface receptor CXCR2 of the embryoid bodies with the CXCR2-specific ligand GRO-α.

BACKGROUND ART

Stem cells refer to cells having not only self-replicating ability but also the ability to differentiate into at least two types of cells, and can be divided into totipotent stem cells, pluripotent stem cells, and multipotent stem cells. In recent years, studies have been actively conducted to treat various diseases with stem cells capable of differentiating into various cells. Thus, the ultimate object of stem cell studies is to make a desired type of cell or tissue for use in technology such as cell therapy or tissue engineering.

Thus, the problem to be solved to use stem cells in actual applications is the development of a technology capable of inducing the differentiation of stem cells into desired cells. Accordingly, studies have been attempted to induce stem cells to differentiate into specific cells, and induced pluripotent stem (iPS) cells produced by reprogramming of somatic cells, etc., have been used in differentiation for cell therapy.

Generally, methods of promotes differentiation are used to induce the differentiation of stem cells. Typical examples of these methods include a method of inducing the differentiation of embryonic stem cells into neurons by using retionic acid (*Dev. Dyn.* 236:3255-3266, 2007), a method of inducing the differentiation of embryonic stem cells into hepatocytes by using activin A (*Nat. Biotechnol.* 23:1534-1541, 2005), a method of inducing the differentiation of embryonic stem cells into cardiomyocytes by using ascorbic acid (*Circulation* 107:1912-1916, 2003), and the like. However, conventional methods have disadvantages in that these methods are expensive due to the use of expensive reagents such as cytokines and show low differentiation rates. Thus, in order to effectively use stem cells in various fields, it is required to develop an inexpensive and easy method capable of inducing the differentiation of stem cells into a desired specific tissue with high differentiation efficiency.

In most vertebrates including humans, three-germ-layer cells (endoderm, mesoderm and ectoderm) are formed through gastrulation of early embryos, and all cells constituting the human body tissue differentiate from the three-germ-layer cells. In the case of embryonic stem cells established in vitro by extracting an inner cell mass from blastocysts that are early embryos, an event similar to gastrulation is observed during the formation of embryoid bodies. The first important step for inducing the differentiation of specific cells from embryonic stem cells is to increase a specific germ layer which is the origin of the target cells to be obtained by differentiation, and inducing the differentiation of desired cells from the three-germ-layer cells will be the most efficient differentiation method. In particular, in order to increase the utility of stem cells as a cell therapeutic agent, a technique of efficiently inducing the differentiation of stem cells into specific cells is required.

Recently, a method of promoting the differentiation of human pluripotent stem cell-derived embryoid bodies by inhibiting their mTOR (mammalian target of rapamycin) (Zhou J et al., *Proc Natl Acad Sci USA.* 106(19):7840-5, 2009) was reported. However, this method is a technique that does not act on a cell receptor, but acts on a signaling protein, and promotes the specific differentiation of embryoid bodies into endoderm or mesoderm. In order to control the differentiation of human pluripotent stem cell-derived embryoid bodies, it is most important to develop a technique that acts on a cell receptor. This is because a technique that acts on a signaling protein or enzyme is highly likely influenced by other intracellular factors that influence signaling or enzymatic activity, compared to a technique that acts on a cell receptor, and because an operation for controlling the degree of differentiation can be relatively difficult. However, controlling the differentiation of human pluripotent stem cell-derived embryoid bodies by use of a cell receptor is not yet known.

Accordingly, the present inventors have made extensive efforts to induce the differentiation of stem cells into desired specific tissue or cells in order to increase the utility of stem cells as a cell therapeutic agent, and as a result, have found that the selective differentiation of human pluripotent stem cell-derived embryoid bodies into ectoderm is promoted by stimulation of CXCR2 receptor, thereby completing the present invention.

DISCLOSURE OF INVENTION

It is an object of the present invention to provide a method for inducing the differentiation of pluripotent stem cells into ectoderm, the method comprising the steps of: (i) forming embryoid bodies from pluripotent stem cells; and (ii) culturing the embryoid bodies in a medium containing a CXCR2 ligand.

Another object of the present invention is to provide a composition for inducing the differentiation of pluripotent stem cell-derived embryoid bodies into ectoderm, the composition containing a CXCR2 ligand as an active ingredient.

To achieve the above objects, the present invention provides a method for inducing the differentiation of pluripotent stem cells into ectoderm, the method comprising the steps of: (i) forming embryoid bodies from pluripotent stem cells; and (ii) culturing the embryoid bodies in a medium containing a CXCR2 ligand.

The present invention also provides a composition for inducing the differentiation of pluripotent stem cell-derived embryoid bodies into ectoderm, the composition containing a CXCR2 ligand as an active ingredient.

Advantageous Effects

The method of inducing the differentiation of human pluripotent stem cell-derived embryoid bodies into ectoderm by CXCR2 stimulation according to the present invention can increase the efficiency and utility of stem cells as a cell therapeutic agent, because it promotes the differentiation of stem cells into a specific germ layer serving as the origin of target cells, which is the first important step for inducing the differentiation of stem cells into specific cells.

BEST MODE FOR CARRYING OUT THE INVENTION

Figure 1:
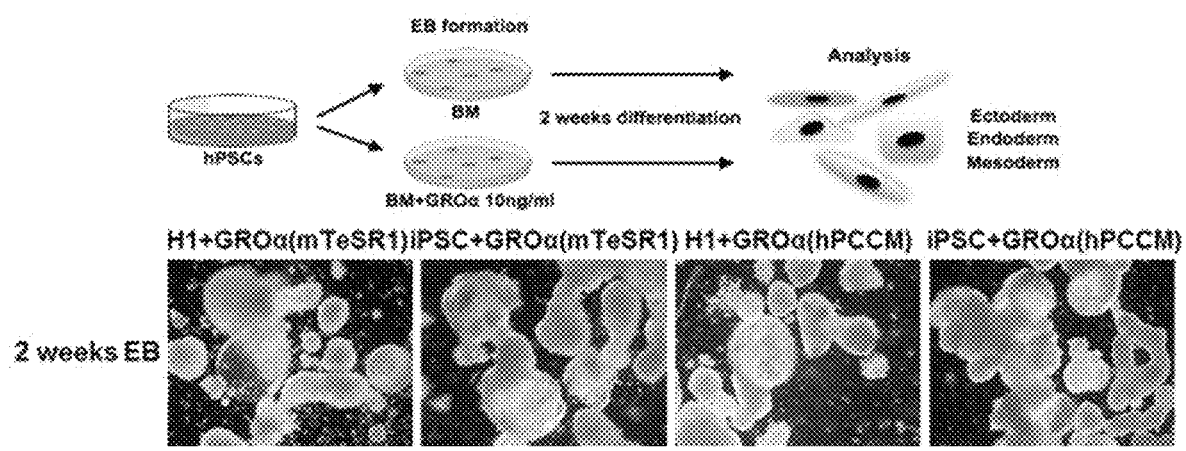
FIG. 1 shows a schematic view of a process in which human pluripotent stem cells (hPSCs) cultured under various conditions are induced to differentiate using GRO-α for 2 weeks, and then a change in gene expression is analyzed by real-time polymerase chain reaction, and also shows the results of observing the appearance of embryoid bodies after 2-week induction of differentiation.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, the surface receptor CXCR2 in human pluripotent stem cell-derived embryoid bodies was activated by stimulation with the CXCR2-specific ligand GRO-α, and then the expression of ectoderm-specific genes such as Nestin, Sox1, Pax6 and Prox1 was analyzed by real-time polymerase chain reaction. As a result, it was found that the differentiation of human pluripotent stem cell-derived embryoid bodies into ectoderm was significantly induced by stimulation of CXCR2.

Thus, in one aspect, the present invention is directed to a method for inducing the differentiation of pluripotent stem cells into ectoderm, the method comprising the steps of: (i) forming embryoid bodies from pluripotent stem cells; and (ii) culturing the embryoid bodies in a medium containing a CXCR2 ligand.

In another aspect, the present invention is directed to a composition for inducing the differentiation of pluripotent stem cell-derived embryoid bodies into ectoderm, the composition containing a CXCR2 ligand as an active ingredient.

In the present invention, the ectoderm preferably expresses one or more genes selected from the group consisting of Nestin, Sox1, Pax6, and Prox1(Kevin A D'Amour et al., *nature biotech* 23:1534-1541, 2005; AKK Teo et al., *Genes & Development* 25(3):238-250, 2011; C Verfaillie et al., *Hematology* 10(S1):293-296, 2005; H Kaspi et al., *Stem Cells* 31(10):2266-72, 2013; P Noisa et al., *PLoS One* 7(5);e37129, 2012), but is not limited thereto. The genes that are expressed in ectoderm and ectodermal tissue include Nestin, beta-tubulin III, MAP-2, a neurofilament heavy chain, dopamine beta hydroxylase, a neural cell adhesion molecule, S-100, Pax-6, neural tubulin and choline acetyltransferase. In addition, other known genes may be used depending on the type of cells. For example, in neural progenitor cells, the expression of genes such as Nestin, Dcx, Sox1, HuD and the like can be observed, and in completely differentiated neurons, the expression of MAP2, NeuN, NF200, NSE and the like can be observed.

CXCR2 (CXC-chemokine receptor 2) is a receptor of conventional chemoattractant.

In the present invention, the "CXCR2 ligand" is binding to the CXCR2 receptor, that means an increased expression of the CXCR2 and activated CXCR2.

In the present invention, the CXCR2 ligand is preferably any one selected from the group consisting of GRO-α, GRO-β, GRO-γ, GCP-2, NAP-2, ENA-78, and IL-8, more preferably GRO-α, but is not limited thereto. In addition, GRO-α is used at a concentration of 5-20 ng/ml, more preferably 10 ng/ml, but is not limited thereto.

Generally, to induce stem cells to differentiate into endodermal, mesodermal or ectodermal cells, a method employing a biochemical agent that induces differentiation in a specific manner for type of endoderm, mesoderm and ectoderm is used. Specifically, in conventional methods, retinoic acid, lithium chloride, basic fibroblast growth factor (bFGF), epidermal growth factor (EGF) or the like is used for differentiation into ectodermal cells, and betacellulin, activin, sonic hedgehog (shh) or the like is used for differentiation into endodermal cells. In addition, dexamethasone, dimethyl sulfoxide, basic fibroblast growth factor, vascular endothelial growth factor (VEGF) or the like is used for differentiation into mesodermal cells. As described above, very diverse drugs are used depending on the direction of differentiation, and various combinations of such biochemical agents for inducing differentiation may also be used. However, as mentioned above, there is a problem in that the rate of differentiation is low despite the use of various biochemical agents as described above. In addition, in most conventional differentiation methods, the viability of cells has become a big problem, because the differentiation process progresses over a long period of time and a large amount of cells die during the differentiation process. Furthermore, the conventional methods are disadvantageous in economic terms, because the above-described bFGF, FGF8, SHH, BDNF and the like are very expensive. However, the induction of differentiation into ectoderm by CXCR2 stimulation according to the present invention is not influenced by a culture medium composition (i.e., the presence or absence of bFGF or CXCR2 ligands) for culturing human pluripotent stem cells.

In the present invention, the culture of embryoid bodies in the medium containing the CXCR2 ligand is preferably performed for 10-20 days, more preferably 14 days, but is not limited.

In the present invention, the pluripotent stem cells are preferably human embryonic stem cells or human induced pluripotent stem (iPS) cells, but are not limited thereto. As used herein, the term "pluripotent stem cells" means stem cells capable of differentiating into three-germ-layer cells (endoderm, mesoderm and ectoderm) (pluripotency), and is preferably intended to include not only embryonic stem cells, but also cells having this capability, among induced pluripotent stem (iPS) cells and adult stem cells.

In the present invention, ectodermal cells that differentiated from stem cell-derived embryoid bodies may differentiate into central nervous system neurons, ganglia, nerves, cranial bone, skin epidermal cells, hair, pigment cells, eye's crystalline lens, corneal cells, conjunctival cells, epithelial cells of sensory organ, lacrimal gland, mammary gland, etc., and each type of the cells may be produced by treating ectodermal cells, which differentiated from the stem cell-derived embryoid bodies of the present invention, under specific differentiation conditions. For example, when growth factors such as EGF and FGF are removed from a culture of neurospheres, the neurospheres differentiate into neurons, astrocytes, oligodendrocytes, etc., which can be transplanted into an injured site in the brain (Kevin A D'Amour et al., *nature biotech* 23:1534-1541, 2005; AKK Teo et al., *Genes & Development* 25(3):238-250, 2011; C Verfaillie et al., *Hematology* 10(S1):293-296, 2005; H Kaspi et al., *Stem Cells* 31(10):2266-72, 2013; P Noisa et al., *PLoS One* 7(5);e37129, 2012).

Because the most time-consuming step in studies on stem cell differentiation is a step of analyzing the effect of a specific culture condition on the induction of differentiation, an effective method capable of inducing stem cells to differentiate into any germ layer is required. Particularly, in order to increase the utility of stem cells as a cell therapeutic agent by excluding the risk of contamination with other substances due to the use of differentiation inducers, a technique of efficiently inducing stem cells to differentiate into specific cells is required.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Induction of Differentiation of Human Pluripotent Stem Cells into Ectoderm

Human pluripotent stem cells are able to differentiate into all types of human cells, and a step of forming embryoid bodies for a specific period of time and determining differentiation into three-germ-layer cells by the stimulation and activation of each of receptors should be performed to induce cell differentiation. However, a significant portion about the induction of lineage-specific differentiation is still required to be developed.

In this Example, in order to induce ectodermal differentiation, human pluripotent stem cells (hPSCs) purchased from WiCell (http://www.wicell.org/) were cultured to form embryoid bodies in a low-attachment 6-well culture dish (Corning, USA) in a floating state, and then differentiation of the embryoid bodies was induced. For induction of differentiation, the CXCR2-specific ligand GRO-a (human recombinant GROα, R&D Systems) was added continuously over 2 weeks at a low concentration of 10 ng/ml to stimulate and activate the surface receptor CXCR2 of the human pluripotent stem cell-derived embryoid bodies, thereby promoting the selective differentiation of embryoid bodies into ectoderm. In this Example, two different stem cell lines, a human embryonic stem cell line (H1) and a human induced pluripotent stem cell (iPSC) line, were used.

Specifically, verification was performed using two different culture conditions and two different stem cell lines. Using a stem cell line, cultured in a culture condition (mTeSR1+Matrigel) including FGF2, that is generally used, as a control, and using a stem cell line, cultured in a medium excluding FGF2, as an experimental group, formation of embryoid bodies in each of the stem cell lines was induced, and the expression of genes was extensively compared between the embryoid bodies cultured in basal medium (BM) to which GRO-α stimulating the CXCR2 receptor was added over 2 weeks, and the embryoid bodies cultured in basal medium to which GRO-α was not added. Because a differentiation induction time of 14 days is not sufficient to induce differentiation into specific lineage cells, selective differentiation into specific cells occurs after the expression of three-germ-layer lineages was generally observed, and a differentiation induction time of one to two months is generally required.

The control and experimental groups shown in FIG. 1 are as follows. mTeSR1+H1: human embryonic stem cells cultured in the control group; mTeSR1+iPSC: human induced pluripotent stem cells cultured in the control group; hPCCM+H1: human embryonic stem cells cultured in the experimental group; hPCCM+iPSC: human induced pluripotent stem cells cultured in the experimental group; mTeSR1+H1+GROα: a group to which the CXCR2-stimulating ligand GROα was added when embryoid bodies derived from the human embryonic stem cells cultured in the control were induced to differentiate; mTeSR1+iPSC+GROα: a group to which CXCR2-stimulating ligand GROα was added when embryoid bodies derived from the human induced pluripotent stem cells cultured in the control were induced to differentiate; and experimental groups treated in the same manner as these groups. In addition, the group induced to differentiate without adding the CXCR2-stimulating ligand GROα to the cells cultured in each of the control and experimental groups was named "control EB (embryoid body)". The reason why the cells cultured under the two conditions were used in the present invention is to demonstrate that the induction of selective differentiation by CXCR2 stimulation is applied not only to cells cultured in a limited culture environment, but also to human pluripotent stem cells cultured under all culture conditions.

Example 2

Analysis of Differentiation into Ectoderm by Real-Time Polymerase Chain Reaction After the induction of differentiation into ectoderm, changes in the expression of Nestin, Sox1, Pax6 and Prox1 genes that are ectoderm-specific expression markers were analyzed by real-time polymerase chain reaction.

Specifically, RNAs were isolated from differentiation-induced cells using a Qiagen RNeasy kit (Qiagen Hilden, Germany), and cDNAs were synthesized using 2 μg of each RNA, oligo (dT) and Superscript II reverse transcriptase (Gibco). Target gene primers and an iQ SYBR Green qPCR Master Mix were added to each of the synthesized cDNAs, and analysis was performed using a Bio-Rad iCycler iQ system (Bio-Rad Laboratories, USA). The results were normalized using the GAPDH gene, and P values were used to determine statistical significance ($*P<0.05$, $P<0.01$, and $*P<0.001$).

Primers used to analyze the expression of ectodermal, endodermal and mesodermal genes are as follows:

(1) Ectoderm gene

NESTIN: GCGTTGGAA CAGAGGTTGGA (SEQ ID NO: 1)/TGGGAGCAAAGATCCAAGAC (SEQ ID NO: 2)

SOX1: CACAACTCG GAG ATC AGCAA (SEQ ID NO: 3)/GGTACTTGTAATCCGGGTGC (SEQ ID NO: 4)

PAX6: CTGGCTAGCGAAAAGCAACAG (SEQ ID NO: 5)/CCCGTTCAACATCCTTAGTTTATCA (SEQ ID NO: 6)

PROX1: GCTCCAATATGCTGAAGACC (SEQ ID NO: 7)/ATCGTTGATGGCTTGACGTG (SEQ ID NO: 8)

(2) Mesoderm gene

T(Brachyury): AATTGGTCC AGCCTTGGAAT (SEQ ID NO: 9)/CGTTGCTCACAGACCACA (SEQ ID NO: 10)

SNAIL2: ACAGCGAACTGGACACACAT (SEQ ID NO: 11)/GATGGGGCTGTATGCTCCT (SEQ ID NO: 12)

MIXL1: GGTACCCCGACATCCACTT (SEQ ID NO: 13)/GCCTGTTCTGGAACCATACCT (SEQ ID NO: 14)

TWIST1: AGCTACGCCTTCTCGGTCT (SEQ ID NO: 15)/CCTTCTCTGGAAACAATGACATC (SEQ ID NO: 16)

MYOCARDIN: TCACTTTCTGCCCTCATCCT (SEQ ID NO: 17)/TCGTGTGCTCCTGAGTTCTG (SEQ ID NO: 18)

Flt1: TCATGAATGTTTCCCTGCAA (SEQ ID NO: 19)/GGAGGTATGGTGCTTCCTGA (SEQ ID NO: 20)

(3) Endoderm gene

AFP: AGAACCTGTCACAAGCTGTG (SEQ ID NO: 21)/GACAGCAAGCTGAGGATGTC (SEQ ID NO: 22)

GATA4: TCCCTCTTCCCTCCTCAAAT (SEQ ID NO: 23)/TCAGCGTGTAAAGGCATCTG (SEQ ID NO: 24)

CXCR4: CCTGCCTGGTATTGTCATCC (SEQ ID NO: 25)/AGGATGACTGTGGTCTTGAGG (SEQ ID NO: 26)

ZO1: GGTCAGAGCCTTCTGATCATTC (SEQ ID NO: 27)/CATCTCTACTCCGGAGACTGC (SEQ ID NO: 28)

SOX17: CAGACTCCTGGGTTTTTGTTGTTGCTG (SEQ ID NO: 29)/GAAATGGAGGAAGCTGTTTTGGGACAC (SEQ ID NO: 30)

Foxa2: TTCTCCATCAACAACCTCATGTCC (SEQ ID NO: 31)/GTAGTGCATCACCTGTTCGTAGG (SEQ ID NO: 32)

Figure 2:
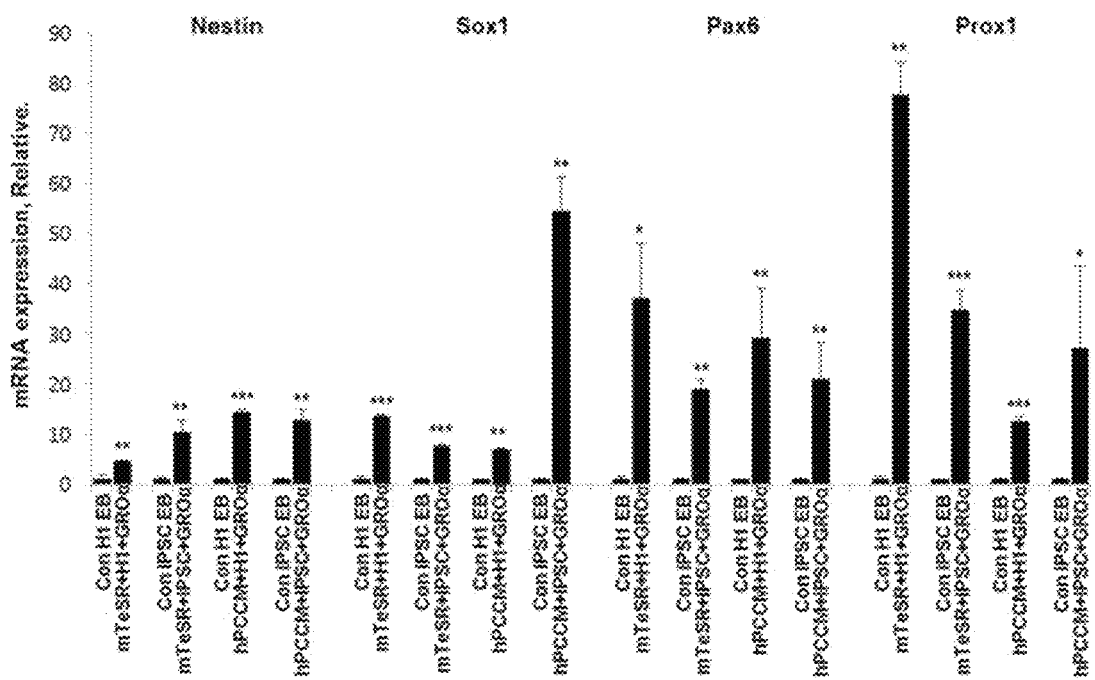
FIG. 2 shows the results of analyzing the expression of ectodermal genes, including Nestin, Sox1, Pax6 and Prox1, by real-time polymerase chain reaction.
Figure 3:
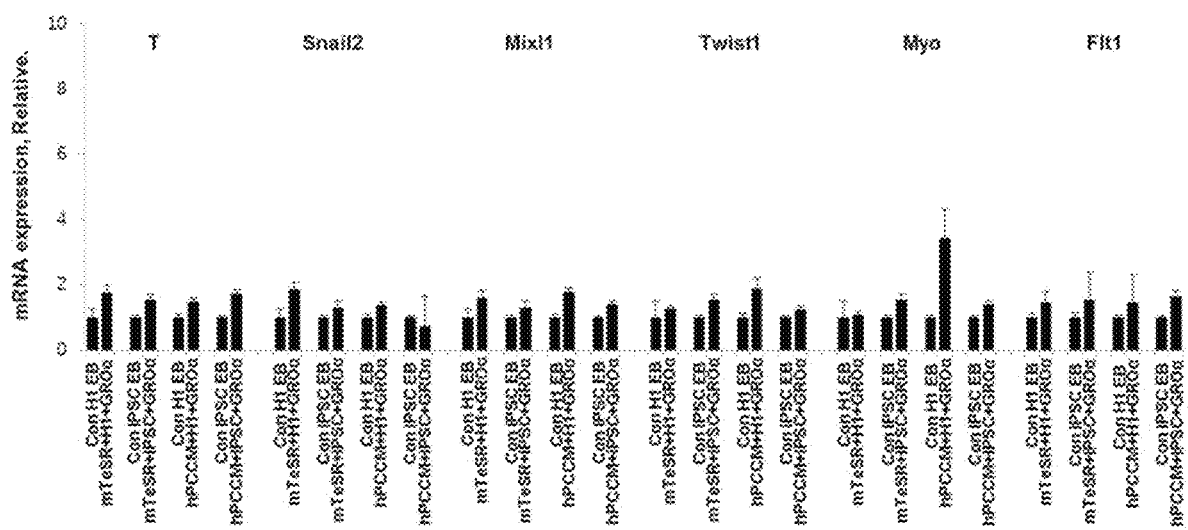
FIG. 3 shows the results of analyzing the expression of mesodermal genes, including T, Snail2, Mixl1, Twist1, Myo and Flt1, by real-time polymerase chain reaction.
Figure 4:
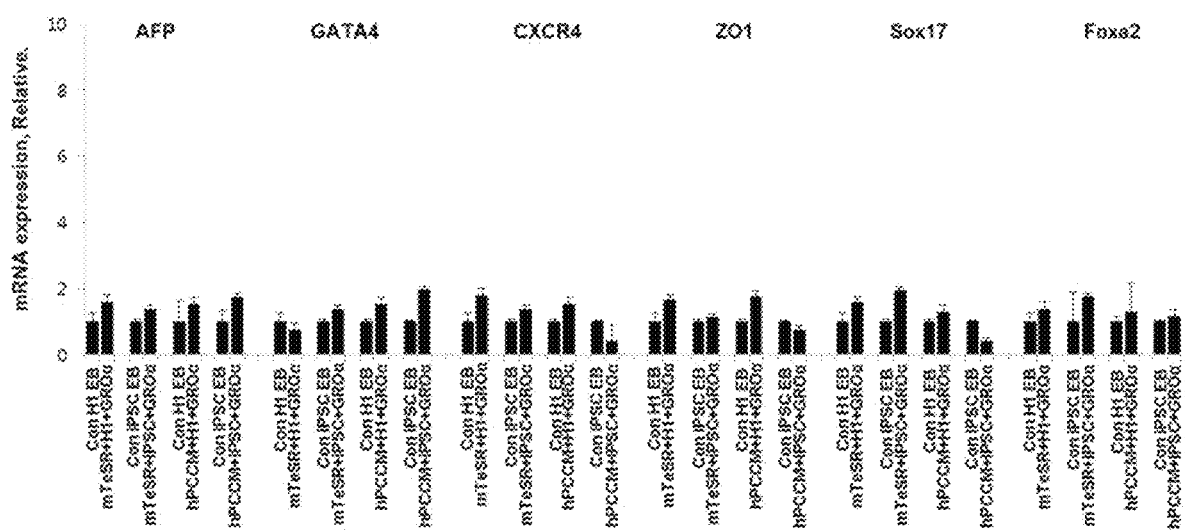
FIG. 4 shows the results of analyzing the expression of endodermal genes, including AFP, GATA4, CXCR4, ZO1, Sox17 and Foxa2, by real-time polymerase chain reaction.
Figure 5:
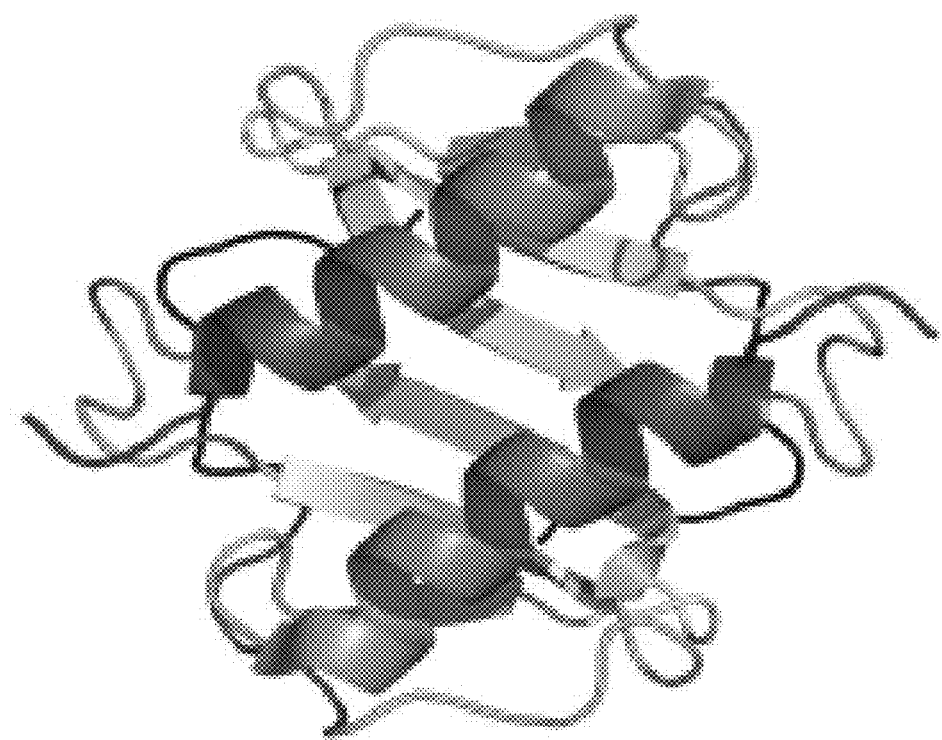
FIG. 5 shows the structure of GRO-α protein (7.9 kDa).

As a result, it was shown that the expression of Nestin, Sox1, Pax6 and Prox1 genes in the experimental group in which CXCR2 was stimulated by treatment with GRO-α was significantly higher than that in the control cells to which GRO-α was not added (FIG. 2). Such results appeared to be identical under all the conditions regardless of the difference in the composition of the culture medium.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method or inducing differentiation of human induced pluripotent stem (iPS) cells into ectoderm, the method comprising the steps of:
   (i) forming embryoid bodies from human induced pluripotent stem (iPS) cells; and
   (ii) culturing the embryoid bodies in a medium comprising GRO-α for 14-20 days to induce differentiation into ectoderm by CXCR2 stimulation,
   wherein the ectoderm expresses Nestin, Sox1, Pax6, and Prox1.

* * * * *

UNITED STATES PATENT AND TRADEMARK OFFICE
CERTIFICATE OF CORRECTION

PATENT NO. : 10,655,100 B2
APPLICATION NO. : 14/936729
DATED : May 19, 2020
INVENTOR(S) : Byung Soo Kim Page 1 of 1

It is certified that error appears in the above-identified patent and that said Letters Patent is hereby corrected as shown below:

On the Title Page

Item [74] "Steven J. Hulquist" should be -- Steven J. Hultquist --.

In the Specification

Column 5, Line 53: "GRO-a" should be -- GRO-α --.

In the Claims

Column 17, Line 24 Claim 1: "or" should be -- for --.

Column 17, Line 25 Claim 1: "stern" should be -- stem --.

Signed and Sealed this
Twenty-first Day of July, 2020

Andrei Iancu
*Director of the United States Patent and Trademark Office*

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: NESTIN-F

<400> SEQUENCE: 1
gcgttggaac agaggttgga                                           20

<210> SEQ ID NO 2
<211> LENGTH: 20
<212> TYPE: DNA
<213> ORGANISM: Artificial Sequence
<220> FEATURE:
<223> OTHER INFORMATION: NESTIN-R

<400> SEQUENCE: 2
tgggagcaaa gatccaagac                                           20

<210> SEQ ID NO 3
<211> LENGTH: 20
<212> TYPE: DNA
<213> ORGANISM: Artificial Sequence
<220> FEATURE:
<223> OTHER INFORMATION: SOX1-F

<400> SEQUENCE: 3
cacaactcgg agatcagcaa                                           20

<210> SEQ ID NO 4
<211> LENGTH: 20
<212> TYPE: DNA
<213> ORGANISM: Artificial Sequence
<220> FEATURE:
<223> OTHER INFORMATION: SOX1-R

<400> SEQUENCE: 4
```

```
ggtacttgta atccgggtgc                                              20

<210> SEQ ID NO 5
<211> LENGTH: 21
<212> TYPE: DNA
<213> ORGANISM: Artificial Sequence
<220> FEATURE:
<223> OTHER INFORMATION: PAX6-F

<400> SEQUENCE: 5
ctggctagcg aaaagcaaca g                                            21

<210> SEQ ID NO 6
<211> LENGTH: 25
<212> TYPE: DNA
<213> ORGANISM: Artificial Sequence
<220> FEATURE:
<223> OTHER INFORMATION: PAX6-R

<400> SEQUENCE: 6
cccgttcaac atccttagtt tatca                                        25

<210> SEQ ID NO 7
<211> LENGTH: 20
<212> TYPE: DNA
<213> ORGANISM: Artificial Sequence
<220> FEATURE:
<223> OTHER INFORMATION: PROX1-F

<400> SEQUENCE: 7
gctccaatat gctgaagacc                                              20

<210> SEQ ID NO 8
<211> LENGTH: 20
<212> TYPE: DNA
<213> ORGANISM: Artificial Sequence
<220> FEATURE:
<223> OTHER INFORMATION: PROX1-R

<400> SEQUENCE: 8
atcgttgatg gcttgacgtg                                              20

<210> SEQ ID NO 9
<211> LENGTH: 20
<212> TYPE: DNA
<213> ORGANISM: Artificial Sequence
<220> FEATURE:
<223> OTHER INFORMATION: T-F

<400> SEQUENCE: 9
aattggtcca gccttggaat                                              20

<210> SEQ ID NO 10
<211> LENGTH: 18
<212> TYPE: DNA
<213> ORGANISM: Artificial Sequence
<220> FEATURE:
<223> OTHER INFORMATION: T-R

<400> SEQUENCE: 10
cgttgctcac agaccaca                                                18

<210> SEQ ID NO 11
<211> LENGTH: 20
<212> TYPE: DNA
```

```
<213> ORGANISM: Artificial Sequence
<220> FEATURE:
<223> OTHER INFORMATION: SNAIL2-R

<400> SEQUENCE: 11
acagcgaact ggacacacat                                               20

<210> SEQ ID NO 12
<211> LENGTH: 19
<212> TYPE: DNA
<213> ORGANISM: Artificial Sequence
<220> FEATURE:
<223> OTHER INFORMATION: SNAIL2-R

<400> SEQUENCE: 12
gatggggctg tatgctcct                                                19

<210> SEQ ID NO 13
<211> LENGTH: 19
<212> TYPE: DNA
<213> ORGANISM: Artificial Sequence
<220> FEATURE:
<223> OTHER INFORMATION: MIXL1-F

<400> SEQUENCE: 13
ggtaccccga catccactt                                                19

<210> SEQ ID NO 14
<211> LENGTH: 21
<212> TYPE: DNA
<213> ORGANISM: Artificial Sequence
<220> FEATURE:
<223> OTHER INFORMATION: MIXL1-R

<400> SEQUENCE: 14
gcctgttctg gaaccatacc t                                             21

<210> SEQ ID NO 15
<211> LENGTH: 19
<212> TYPE: DNA
<213> ORGANISM: Artificial Sequence
<220> FEATURE:
<223> OTHER INFORMATION: TWIST1-F

<400> SEQUENCE: 15
agctacgcct tctcggtct                                                19

<210> SEQ ID NO 16
<211> LENGTH: 23
<212> TYPE: DNA
<213> ORGANISM: Artificial Sequence
<220> FEATURE:
<223> OTHER INFORMATION: TWIST1-R

<400> SEQUENCE: 16
ccttctctgg aaacaatgac atc                                           23

<210> SEQ ID NO 17
<211> LENGTH: 20
<212> TYPE: DNA
<213> ORGANISM: Artificial Sequence
<220> FEATURE:
<223> OTHER INFORMATION: MYOCARDIN-F

<400> SEQUENCE: 17
tcactttctg ccctcatcct                                               20
```

<210> SEQ ID NO 18
<211> LENGTH: 20
<212> TYPE: DNA
<213> ORGANISM: Artificial Sequence
<220> FEATURE:
<223> OTHER INFORMATION: MYOCARDIN-R

<400> SEQUENCE: 18
tcgtgtgctc ctgagttctg                                           20

<210> SEQ ID NO 19
<211> LENGTH: 20
<212> TYPE: DNA
<213> ORGANISM: Artificial Sequence
<220> FEATURE:
<223> OTHER INFORMATION: Flt1-F

<400> SEQUENCE: 19
tcatgaatgt ttccctgcaa                                           20

<210> SEQ ID NO 20
<211> LENGTH: 20
<212> TYPE: DNA
<213> ORGANISM: Artificial Sequence
<220> FEATURE:
<223> OTHER INFORMATION: Flt1-R

<400> SEQUENCE: 20
ggaggtatgg tgcttcctga                                           20

<210> SEQ ID NO 21
<211> LENGTH: 20
<212> TYPE: DNA
<213> ORGANISM: Artificial Sequence
<220> FEATURE:
<223> OTHER INFORMATION: AFP-F

<400> SEQUENCE: 21
agaacctgtc acaagctgtg                                           20

<210> SEQ ID NO 22
<211> LENGTH: 20
<212> TYPE: DNA
<213> ORGANISM: Artificial Sequence
<220> FEATURE:
<223> OTHER INFORMATION: AFP-R

<400> SEQUENCE: 22
gacagcaagc tgaggatgtc                                           20

<210> SEQ ID NO 23
<211> LENGTH: 20
<212> TYPE: DNA
<213> ORGANISM: Artificial Sequence
<220> FEATURE:
<223> OTHER INFORMATION: GATA4-F

<400> SEQUENCE: 23
tccctcttcc ctcctcaaat                                           20

<210> SEQ ID NO 24
<211> LENGTH: 20
<212> TYPE: DNA
<213> ORGANISM: Artificial Sequence
<220> FEATURE:

```
<223> OTHER INFORMATION: GATA4-R

<400> SEQUENCE: 24
tcagcgtgta aaggcatctg                                               20

<210> SEQ ID NO 25
<211> LENGTH: 20
<212> TYPE: DNA
<213> ORGANISM: Artificial Sequence
<220> FEATURE:
<223> OTHER INFORMATION: CXCR4-F

<400> SEQUENCE: 25
cctgcctggt attgtcatcc                                               20

<210> SEQ ID NO 26
<211> LENGTH: 21
<212> TYPE: DNA
<213> ORGANISM: Artificial Sequence
<220> FEATURE:
<223> OTHER INFORMATION: CXCR4-R

<400> SEQUENCE: 26
aggatgactg tggtcttgag g                                             21

<210> SEQ ID NO 27
<211> LENGTH: 21
<212> TYPE: DNA
<213> ORGANISM: Artificial Sequence
<220> FEATURE:
<223> OTHER INFORMATION: ZO1-F

<400> SEQUENCE: 27
ggtcagagcc ttctgatcat t                                             21

<210> SEQ ID NO 28
<211> LENGTH: 21
<212> TYPE: DNA
<213> ORGANISM: Artificial Sequence
<220> FEATURE:
<223> OTHER INFORMATION: ZO1-R

<400> SEQUENCE: 28
catctctact ccggagactg c                                             21

<210> SEQ ID NO 29
<211> LENGTH: 27
<212> TYPE: DNA
<213> ORGANISM: Artificial Sequence
<220> FEATURE:
<223> OTHER INFORMATION: SOX17-F

<400> SEQUENCE: 29
cagactcctg ggtttttgtt gttgctg                                       27

<210> SEQ ID NO 30
<211> LENGTH: 27
<212> TYPE: DNA
<213> ORGANISM: Artificial Sequence
<220> FEATURE:
<223> OTHER INFORMATION: SOX17-R

<400> SEQUENCE: 30
gaaatggagg aagctgtttt gggacac                                       27
```

```
<210> SEQ ID NO 31
<211> LENGTH: 24
<212> TYPE: DNA
<213> ORGANISM: Artificial Sequence
<220> FEATURE:
<223> OTHER INFORMATION: Foxa2-F

<400> SEQUENCE: 31
ttctccatca acaacctcat gtcc                                          24

<210> SEQ ID NO 32
<211> LENGTH: 23
<212> TYPE: DNA
<213> ORGANISM: Artificial Sequence
<220> FEATURE:
<223> OTHER INFORMATION: Foxa2-R

<400> SEQUENCE: 32
gtagtgcatc acctgttcgt agg                                           23
```